(12) United States Patent
Rudolph et al.

(10) Patent No.: US 7,897,567 B2
(45) Date of Patent: Mar. 1, 2011

(54) METHODS OF PROTECTING AGAINST RADIATION DAMAGE USING ALPHA THYMOSIN

(75) Inventors: Alfred R. Rudolph, Los Altos Hills, CA (US); Cynthia W. Tuthill, Menlo Park, CA (US)

(73) Assignee: SciClone Pharmaceuticals, Inc., Foster City, CA (US)

( * ) Notice: Subject to any disclaimer, the term of this patent is extended or adjusted under 35 U.S.C. 154(b) by 365 days.

(21) Appl. No.: 10/535,835

(22) PCT Filed: Nov. 25, 2003

(86) PCT No.: PCT/US03/37469
§ 371 (c)(1),
(2), (4) Date: Oct. 19, 2005

(87) PCT Pub. No.: WO2004/048971
PCT Pub. Date: Jun. 10, 2004

(65) Prior Publication Data
US 2006/0166877 A1    Jul. 27, 2006

Related U.S. Application Data

(60) Provisional application No. 60/428,746, filed on Nov. 25, 2002.

(51) Int. Cl.
*A61K 38/00* (2006.01)
(52) U.S. Cl. ............................................. 514/12; 514/2
(58) Field of Classification Search ................... None
See application file for complete search history.

(56) References Cited

U.S. PATENT DOCUMENTS

| | | | |
|---|---|---|---|
| 4,079,127 A | 3/1978 | Goldstein et al. | |
| 4,179,337 A | 12/1979 | Davis et al. | |
| 4,353,821 A | 10/1982 | Birr et al. | |
| 5,585,352 A * | 12/1996 | Goldstein et al. | 514/12 |
| 6,197,751 B1 | 3/2001 | Malinda et al. | |
| 6,309,633 B1 | 10/2001 | Ekwuribe et al. | |
| 2005/0049191 A1 | 3/2005 | Ruldolph et al. | |

FOREIGN PATENT DOCUMENTS

| | | |
|---|---|---|
| CN | 1303713 A | 7/2001 |
| GB | 1195980 A | 6/1970 |
| WO | 94/13314 A1 | 6/1994 |
| WO | 0182949 | 11/2001 |
| WO | 0236169 | 5/2002 |
| WO | WO 03/037272 A2 | 5/2003 |

OTHER PUBLICATIONS

Auger et al. The Journal of Histochemistry and Cytochemistry, vol. 35, No. 2, pp. 181-187, 1987.*
Caldarella et al. (PNAS, vol. 80, Dec. 1983, pp. 7424-7427).*
Belyakov et al., "Serum Alpha-1-Thymosin Level and T-Lymphocyte Population Composition in Irradiated Subjects at Late Periods After Radiation Accident," Immunologiya, No. 2, 1992, pp. 30-33.
Gray et al., "Thymosin Alpha1 (Ta-1) Modulation of Irradiation-Induces Cellular Immune Deficiency," Proceedings of the American Association for Cancer Research, vol. 26, Mar. 1985, p. 1106, XP009095398.
Ishitsuka et al., "Efficacy of Thymosin Alpha1 in Animal Models" Thymic Hormones and Lymphokines: Basic Chemical and Clinical Applications, 1984, pp. 925-438.
Schulof et al., "Synthetic Thymosin Alpha1 Following Mediastinal Irradiation: A Randomized Trial in Patients With Locally Advanced Non-Small Cell Lung Cancer," Proceedings of the American Society of Clinical Oncology (Asco Abstracts, Clinical Trials: Lung), vol. 2, Mar. 1983, p. 185, XP009104106.
Shmelev et al., "Thymosin Alpha-1 and Hybrid Proteins Consisting of Tumor Necrosis Factor-Alpha and Thymosin Alpha-1 Enchance the Efficacy of Vaccination Against the Causative Agent of Plague." Zhurnal Mikrobiologii, Epidemiologii, I Immunobiologii, No. 4, Jul. 1994-Aug. 1994, pp. 85-89.
Doria, et al., "Radiation Damage and Recovery of the Immune System" Eur Report, Commission of the European Communities, 1984, EUR-9088, p. 524-527.
Ishitsuka, H. et al., "Efficacy of Thymosin alpha 1in animal models" Thymic hormones and lymphokines: basic chemistry and clinical applications, xx, xx, 1984, pp. 425-438.
JP Application 555637/2004 Office Action mailed Jan. 5, 2010.
NO Application 20052943 mailed Oct. 27, 2009 with English translation.
PO Application P 377376 Office Action dated Mar. 10, 2010.
Vavrova, J., et al., "The Effect of Thymic Humoral Factor upon Regeneration of Lymphatic and Haemopoietic Tissues of Irradiated Mice" 1975, Folia Biologica, 21(4) 238-243.
Vavrova, J., et al., "The Effect of Thymosin Application upon Radiation Sickness in Mice" 1976, Folia Biologica, 22 (5), 320-329.

* cited by examiner

*Primary Examiner* — Hope A Robinson
(74) *Attorney, Agent, or Firm* — Cooley LLP

(57) ABSTRACT

Damage to cells and/or a subject caused by radiation is treated or prevented by administration of an alpha thymosin peptide.

21 Claims, No Drawings

METHODS OF PROTECTING AGAINST RADIATION DAMAGE USING ALPHA THYMOSIN

CROSS-REFERENCE TO RELATED APPLICATION

This application is a National Phase of International Application No. PCT/US03/37469, filed Nov. 25, 2003, which claims the benefit of U.S. Provisional Application No. 60/428,746, filed Nov. 25, 2002.

BACKGROUND OF THE INVENTION

1. Field of the Invention

The present invention relates to the field of protecting a subject, such as a mammal, and/or cells thereof, against radiation damage, or treatment of damage caused by radiation.

2. Description of the Background Art

Persons and their cells can be exposed to radiation during treatment for cancer, and inadvertent or malicious exposure to radiation, such as during nuclear accidents, wartime or terrorist nuclear attack. There are various preparations known in the art for the treatment of radiation damage, and there have been many attempts to treat damage caused by radiation exposure.

There remains a need in the art for improved methods and compositions for healing or preventing the damage caused by exposure to radiation.

SUMMARY OF THE INVENTION

In accordance with the present invention, a method of protecting a subject and/or cells of the subject, against radiation damage, involves administering to a subject in need of such treatment a radiation-protecting and/or radiation-treating amount of an alpha thymosin peptide.

DETAILED DESCRIPTION OF THE INVENTION

The present invention is based on a discovery that alpha thymosin peptides protect a subject and/or cells of the subject against radiation damage. The invention is applicable to conditions in which the subject or cells are exposed to radiation, and the subject is treated prior to the exposure, such as during cancer treatment. The invention also can be applicable to conditions in which the applicant is exposed to the radiation and treated after the exposure (such as during nuclear accidents, wartime or terrorist nuclear attack). The invention is applicable to the protection or treatment of damage caused by both ionizing and non-ionizing radiation.

Thymosins are a class of polypeptide immune modifiers derived from the thymus gland. The thymosins have been shown to trigger maturational events in lymphocytes, to augment T-cell function and to promote reconstitution of immune defects. Thymosin alpha 1 (sometimes referred to as TA1) is a 28-amino acid thymic peptide with a molecular weight of 3100, with immunomodulatory properties, homologous to a natural product originally isolated from thymosin fraction 5 of calf thymus. Its biological effects include augmentation of T lymphocyte functions and include modulation of interleukin-2 (IL-2), stimulation of interferon production, induction of T lymphocytes and NK cell activity, and stimulation of thymopoiesis. Thymosin alpha 1 also has been shown to up-regulate MHC Class I expression.

In accordance with one embodiment, the invention is a method of treatment for protecting cells of a subject against radiation damage, comprising administering to a subject in need of such treatment a composition comprising a radiation-protecting amount of an alpha thymosin peptide.

Alpha thymosin peptides comprise thymosin alpha 1 (TA1) peptides including naturally occurring TA1 as well as synthetic TA1 and recombinant TA1 having the amino acid sequence of naturally occurring TA1, amino acid sequences substantially similar thereto, or an abbreviated sequence form thereof, and their biologically active analogs having substituted, deleted, elongated, replaced, or otherwise modified sequences which possess bioactivity substantially similar to that of TA1, e.g., a TA1 derived peptide having sufficient amino acid homology with TA1 such that it functions in substantially the same way with substantially the same activity as TA1. A preferred alpha thymosin peptide is thymosin alpha 1.

Administration can be by any suitable method, including injection, periodic infusion, continuous infusion, and the like.

Because the plasma half-life of subcutaneously injected TA1 is only about two hours, according to one embodiment, an alpha thymosin peptide such as TA1 is administered to a patient so as to substantially continuously maintain an effective amount of the alpha thymosin peptide in the patient's circulatory system during a substantially longer treatment period. Although much longer treatment periods are contemplated in accordance with the present invention, embodiments of the invention include substantially continuously maintaining an effective amount of the alpha thymosin peptide in the patient's circulatory system during treatment periods of at least about 6, 10, 12 hours, or longer. In other embodiments, treatment periods are for at least about a day, and even for a plurality of days, e.g., a week or longer. However, it is contemplated that treatments, as defined above, in which effective amounts of the alpha thymosin peptide are substantially continuously maintained in the patient's circulatory system, may be separated by non-treatment periods of similar or different durations.

In accordance with one embodiment, the alpha thymosin peptide is continuously infused into a patient, e.g., by intravenous infusion, during the treatment period, so as to substantially continuously maintain an effective amount of the alpha thymosin peptide in the patient's circulatory system. The infusion may be carried out by any suitable means, such as by minipump.

Alternatively, an injection regimen of the alpha thymosin peptide can be maintained so as to substantially continuously maintain an effective amount of the alpha thymosin peptide in the patient's circulatory system. Suitable injection regimens may include an injection every 1, 2, 4, 6, etc. hours, so as to substantially continuously maintain an effective amount of the thymosin peptide in the patient's circulatory system during the treatment period.

Although it is contemplated that during continuous infusion of the alpha thymosin peptide, administration will be for a substantially longer duration, according to one embodiment the continuous infusion of the alpha thymosin peptide is for a treatment period of at least about 1 hour. More preferably, continuous infusion is carried out for longer periods, such as for periods of at least about 6, 8, 10, 12 hours, or longer. In other embodiments, continuous infusion is for at least about one day, and even for a plurality of days such as for one week or more.

In preferred embodiments, the alpha thymosin peptide is present in a pharmaceutically acceptable liquid carrier, such as water for injection, saline in physiological concentrations, or similar.

The present invention also comprises administration of a physiologically active conjugate comprising an alpha thymosin peptide conjugated to a material which increases half-life of the alpha thymosin peptide in serum of a patient when said conjugate is administered to a patient. The material may be a substantially non-antigenic polymer. Suitable polymers will have a molecular weight within a range of about 200-300,000, preferably within a range of about 1,000-100,000, more preferably within a range of about 5,000-35,000, and most preferably within a range of about 10,000-30,000, with a molecular weight of about 20,000 being particularly preferred.

The polymeric substances included are also preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Among the substantially non-antigenic polymers, mono-activated, alkyl-terminated polyalkylene oxides (PAO's), such as monomethyl-terminated polyethylene glycols (mPEG's) are contemplated. In addition to mPEG, C1-4 alkyl-terminated polymers may also be useful.

As an alternative to PAO-based polymers, effectively non-antigenic materials such as dextran, polyvinyl pyrrolidones, polyacrylamides, polyvinyl alcohols, carbohydrate-based polymers and the like can be used. Persons of ordinary skill in the art will realize that the foregoing list is merely illustrative and that all polymer materials having the qualities described herein are contemplated. For purposes of the present invention, "effectively non-antigenic" means all materials understood in the art as being nontoxic and not eliciting an appreciable immunogenic response in mammals.

The polymer may be straight-chain or branched. Polyethylene glycol (PEG) is a particularly preferred polymer.

The polymer can be conjugated to the alpha thymosin peptide by any suitable method. Exemplary methods for conjugating polymers to peptides are disclosed in U.S. Pat. Nos. 4,179,337, 4,766,106, 4,917,888, 5,122,614 and 6,177,074, as well as PCT International Publication No. WO 95/13090, all of which are incorporated herein by reference.

Thymosin alpha 1 has five separate possible sites for amino group conjugation of a polymer, and polymer(s) can be conjugated at one or a plurality of sites.

According to one embodiment, 40,000 molecular weight PEG is conjugated to the N-terminal end of an alpha thymosin peptide, such as thymosin alpha 1 (TA1). This can be formed by solid phase peptide synthesis on insoluble polymeric support beads, as is known in the art, with appropriate side chain protective groups.

After complete synthesis of the alpha thymosin peptide on the beads, the protected peptide is cleaved from the beads leaving the N-terminus with a free amino group, which is reacted with 40,000 molecular weight PEG. The side chain protective groups then are removed to form a conjugate in accordance with this embodiment of the invention.

The isolation, characterization and use of the alpha thymosin peptide thymosin alpha 1 (TA1) is described, for example, in U.S. Pat. No. 4,079,127, U.S. Pat. No. 4,353,821, U.S. Pat. No. 4,148,788 and U.S. Pat. No. 4,116,951.

Suitable dosages of alpha thymosin peptides may be administered in amounts as high as 16 mg/kg body weight/day, or higher. Preferred dosages of alpha thymosin peptide are in the range of about 0.001 mg/kg body weight/day to about 10 mg/kg body weight/day, with an exemplary dose being about 0.02 mg/kg body weight/day.

According to one embodiment, radiation-protecting effective amounts are at dosages which include the alpha thymosin peptide in an amount within the range of about 0.1-10 mg, preferably about 1-5 mg. Further exemplary dosages include the alpha thymosin peptide in an amount of about 1.6 mg and 3.2 mg.

The above dosages reflect only the alpha thymosin peptide present in the composition, and not the weight of the polymer conjugated thereto.

In preferred embodiments, the alpha thymosin peptide is present in a pharmaceutically acceptable liquid carrier, such as water for injection. However, pharmaceutical dosage units containing the alpha thymosin peptide may be formulated in any suitable manner for administration by any suitable route.

When administered to a subject prior to exposure to radiation, the alpha thymosin peptide preferably is administered to the subject at least about 3 hours prior to irradiation. In certain embodiments, the alpha thymosin peptide is administered to the subject a plurality of times prior to irradiation, e.g., 2, 3, 4 or more times prior to irradiation.

When administered to a subject after irradiation, the alpha thymosin peptide preferably is administered as soon as possible after radiation, and preferably administered a plurality of times after irradiation. For example, the alpha thymosin peptide may be administered immediately after irradiation, and every 2, 3, 4, 5 or 6 hours, 3 times per day, twice per day, daily, 3 times per week, twice per week, once per week, etc. Administration can be by injection, infusion or other method.

In accordance with this embodiment, the invention is a method of treatment wherein the alpha thymosin peptide is administered to this subject for promoting healing of radiation damage to cells of the subject.

The subject to be treated may be any mammalian subject exposed to or to be exposed to radiation, such as human subjects or patients.

The invention is further illustrated by the following example, which is not intended to be limiting.

EXAMPLE I

Radiation exposure may damage or kill cells. Therefore, stem and clonogenic cells of the small intestine were exposed to radiation, treated and monitored to observe the effectiveness of the treatment. There are thought to be between four and sixteen actual stem cells in each crypt of the small intestine. There are also a further reserve of clonogneic cells which are capable of regenerating the crypt when all the actual stem cells have been killed. The survival of these clonogenic cells is therefore key to the survival of the crypt and the restoration of an intact epithelial lining following cytotoxic injury (only one clonogenic cell need survive to ensure the survival of the crypt, and therefore maintenance of an intact epithelium). Growth factors and related molecules can be used to manipulate the sensitivity of these cells to cytotoxic agents, and thereby reduce the severity of gastrointestinal and oral mucositis. Factors given prior to a cytotoxic insult may increase clonogenic cell number (thereby increasing the probability of clonogen survival) or act to arrest the cell cycle in such cells (thereby making them more resistant to damage or death). Factors given after the insult may initiate early stem cell amplification or proliferation and hence speed up the regeneration process. A combination of both protocols could give maximum protection to the epithelium. This project therefore examines the effectiveness of thymosin or protecting clonogenic cells, and hence crypts, from radiation induced damage.

36 adult male BDF1 mice (aged 10-12 weeks) were used. The animals were divided into 6 groups and were treated as follows: (1) Control mice, (2) Irradiated, untreated mice, (3) Mice receiving 3 mg/kg thymosin ip 3 hrs prior to irradiation, (4) Mice receiving vehicle ip 3 hrs prior to irradiation, (5) Mice receiving 3 mg/kg thymosin ip 3 times daily for 3 days prior to irradiation, (6) Mice receiving vehicle ip 3 times daily for 3 days prior to irradiation.

The injections were given at 9:00 (3 times treatment) or 12:00 (1 time treatment). At 3:00 on day 3, intestinal damage was induced using a single dose of 13Gy (Gray) X-irradiation.

4 days after irradiation the animals were culled. The small intestine was removed and fixed in Carnoy's fixative prior to processing for histological analysis. 3 um sections were cut and stained with haematoxylin and eosin. Surviving crypts with one or more clonogenic cells are clearly visible in the irradiated sections. Other than those areas, the mesenchyme is entirely denuded-these animals would develop diarrhea and die due to mucositis if allowed to live beyond four days.

For each animal ten intestinal circumferences were analyzed (60 per group). A circumference is equivalent to a given length of intestine and therefore a convenient baseline unit of length. The number of surviving crypts per circumference were scored and the average per group determined. Only crypts containing 10 or more strongly H&E stained cells (excluding Paneth cells) and only intact circumference not containing Peyers patches were scored (Peyers patches influence both the number of crypts in a normal circumference and the ability of a crypt to survive insult).

The average crypt width (measured at its widest point) was also measured in order to correct for scoring errors due to crypt size difference. The correction as applied thus: Corrected number of crypts/circumference=Mean crypt width in untreated control/Mean crypt width in treated animal×Mean number of surviving crypts in treatment group.

All of the animals survived the treatment and exhibited no obvious adverse effects. In the single dose thymosin group the survival levels were similar to the single dose vehicle group. One animal in the vehicle group was slightly less sensitive to the radiation, having more crypts survive (7.9, corrected), increasing the corrected group mean from 2.4 to 3.5. If this animal were excluded there would be a hint of a protective effect with one dose of thymosin (2.4 vs. 3.3). However, since there is a similar variation in crypt survival in the 13Gy alone group, and the triple dose vehicle group has a mean of 3.0, the effect of single dose treatment may be small or negligible.

The triple dose thymosin treatment is of particular interest. A corrected crypt survival of 5.3 compared to 3 in the control was seen, equating to a protection factor of 1.77 (77% increase in surviving crypts).

The invention claimed is:

1. A method for protecting cells of a subject against radiation damage, comprising:

administering to said subject prior to radiation exposure an effective amount of thymosin alpha 1 (TA1) to protect said cells against radiation damage, wherein the effective amount is from about 0.001 to 10 mg/kg body weight, and exposing said subject to radiation.

2. The method of claim 1, wherein the TA1 is recombinant or synthetic.

3. The method of claim 1, wherein the TA1 is administered to said subject at a dosage of about 1-5 mg.

4. The method of claim 1, wherein the TA1 is administered at a dosage of about 1.6 mg.

5. The method of claim 1, wherein the TA1 is administered at a dosage of about 3.2 mg.

6. The method of claim 1, wherein the TA1 is administered at least about 3 hours prior to irradiation.

7. The method of claim 1, wherein the TA1 is administered a plurality of times prior to irradiation.

8. The method of claim 1, wherein the TA1 is administered at least about 3 times prior to irradiation.

9. The method of claim 1, wherein the TA1 is administered to said subject for promoting healing of radiation damage to cells of said subject.

10. The method of claim 9, wherein the TA1 is recombinant.

11. The method of claim 9, wherein the TA1 is administered to said patient at a dosage of about 1-5 mg.

12. The method of claim 9, wherein the TA1 is administered at a dosage of about 1.6 mg.

13. The method of claim 9, wherein the TA1 is administered at a dosage of about 3.2 mg.

14. The method of claim 1, wherein said TA1 is administered by injection or infusion.

15. The method of claim 9, wherein said TA1 is administered by injection or infusion.

16. The method of claim 14, wherein said TA1 is conjugated to a water soluble polymer to increase the plasma half-life of the TA1 in said subject and wherein the water soluble polymer is selected from the group consisting of polyalkylene oxide homopolymers, polyoxyethylenated polyols, copolymers thereof and block copolymers thereof.

17. The method of claim 15, wherein said TA1 is conjugated to a water soluble polymer to increase the plasma half-life of the TA1 in said subject and wherein the water soluble polymer is selected from the group consisting of polyalkylene oxide homopolymers, polyoxyethylenated polyols, copolymers thereof and block copolymers thereof.

18. The method of claim 16, wherein the polymer is PEG.

19. The method of claim 17, wherein the polymer is PEG.

20. The method of claim 1, wherein the TA1 is synthetic.

21. The method of claim 9, wherein the TA1 is synthetic.

* * * * *